United States Patent
Suddaby

(10) Patent No.: US 6,837,850 B2
(45) Date of Patent: Jan. 4, 2005

(54) PERCUTANEOUS TISSUE DISSECTION

(76) Inventor: Loubert Suddaby, 76 Tanglewood Dr., Orchard Park, NY (US) 14127

( * ) Notice: Subject to any disclaimer, the term of this patent is extended or adjusted under 35 U.S.C. 154(b) by 14 days.

(21) Appl. No.: 10/440,411

(22) Filed: May 19, 2003

(65) Prior Publication Data

US 2004/0030222 A1 Feb. 12, 2004

Related U.S. Application Data

(63) Continuation-in-part of application No. 10/143,791, filed on May 14, 2002, now abandoned.

(51) Int. Cl.[7] ................................................ A61B 1/32
(52) U.S. Cl. .................... 600/207; 606/192; 600/204
(58) Field of Search ................................ 606/192, 198, 606/195, 79; 604/105; 600/204, 205, 206, 207, 208, 209, 211

(56) References Cited

U.S. PATENT DOCUMENTS

| 5,522,790 A | | 6/1996 | Moll et al. |
| 5,893,866 A | * | 4/1999 | Hermann et al. ........... 606/192 |
| 2002/0013601 A1 | | 1/2002 | Nobles et al. |

* cited by examiner

Primary Examiner—Kevin Shaver
Assistant Examiner—Candice C. Stokes
(74) Attorney, Agent, or Firm—Shoemaker and Mattare

(57) ABSTRACT

Tissue is retracted from a bone during spinal and other procedures by inserting an elongate balloon into a cannula, and guiding the cannula into position along between the tissue and the bone surface. The cannula is then partially withdrawn, and the balloon is inflated to retract the tissues. The method can be performed percutaneously, with minimal tissue damage.

3 Claims, 4 Drawing Sheets

PERCUTANEOUS TISSUE DISSECTION

This application is a continuation-in-part of application Ser. No. 10/143,791, filed May 14, 2002 now abandoned.

BACKGROUND OF THE INVENTION

This invention relates to a surgical method, specifically to a balloon-assisted method of achieving a percutaneous posterior or posterolateral spinal fusion, or percutaneous surgical repair of bone fractures.

Of all animals having a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change and as such has not benefitted from natural selection as much as have backbones held in the horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five in the low back or lumbar region. There are also five bones in the pelvis or sacral region which are normally fused together and form the back part of the pelvis. This column of bones is critical for protecting the delicate spinal cord and nerves, and for providing structural support for the entire body.

Between the vertebral bones themselves there exist soft tissue structures—discs—composed of fibrous tissue and cartilage. The discs are compressible and act as shock absorbers for sudden downward forces on the upright column. More importantly, the discs allow the bones to move independently of each other to permit functional mobility of the column of spinal vertebrae. Unfortunately, the repetitive forces acting on these intervertebral discs during repetitive day-to-day activities of bending, lifting and twisting cause them to break down or degenerate over time.

Presumably because of humans' upright posture, their intervertebral discs have a high propensity to degenerate. Overt trauma, or covert trauma occurring in the course of repetitive activities disproportionately affect more highly mobile areas of the spine. Disruption of a disc's internal architecture leads to bulging, herniation or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal instability such as spinal curvature or lithesis.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

Present methods of fusing the spine from a posterior or posterolateral approach involve making a midline incision over the spinal elements to be fused. The muscles of the spine are then dissected away from the bony vertebral elements with sharp implements or electro cautery and the free muscle tissue is then retracted laterally with great force to expose the vertebral elements to be fused. The process utilized is very traumatic to the muscle tissues and frequently results in considerable blood loss. A long unsightly midline scar is the long-term consequence of such a spinal operation. Atrophy or scarring and fibrosis of the retracted muscle tissue frequently occurs.

SUMMARY OF THE INVENTION

An object of this invention is to provide a less traumatic method of fusing spinal elements whereby a lengthy incision and traumatic dissection process is not required. Utilizing the process described, both instrumented (pedicle screw) and non-instrumented fusions can be accomplished percutaneously with the assistance of an endoscope to provide light and visualization.

It is also an objective of this invention to provide a method of plating bone fractures percutaneously via endoscopy without need for a lengthy incision.

These and other objects are satisfied by the invention described below.

DESCRIPTION OF THE PREFERRED EMBODIMENT

Figure 1:
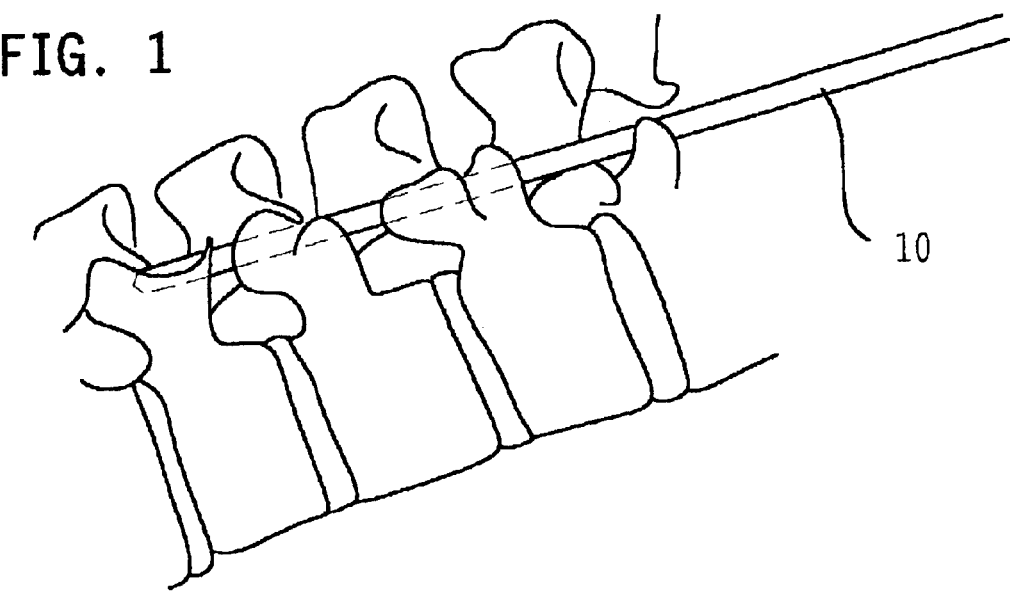
FIG. 1 is a lateral view of the lumbar spine with a metal cannula and internal stylet in place.
Figure 2:
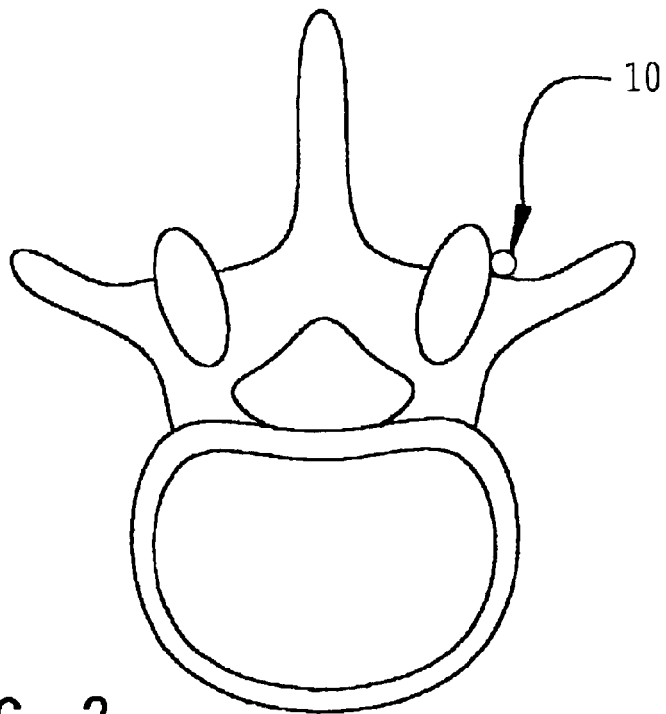
FIG. 2 is an axial view of the spine with the metal cannula and internal stylet in place adjacent to a facet and above the transverse process.
Figure 3:
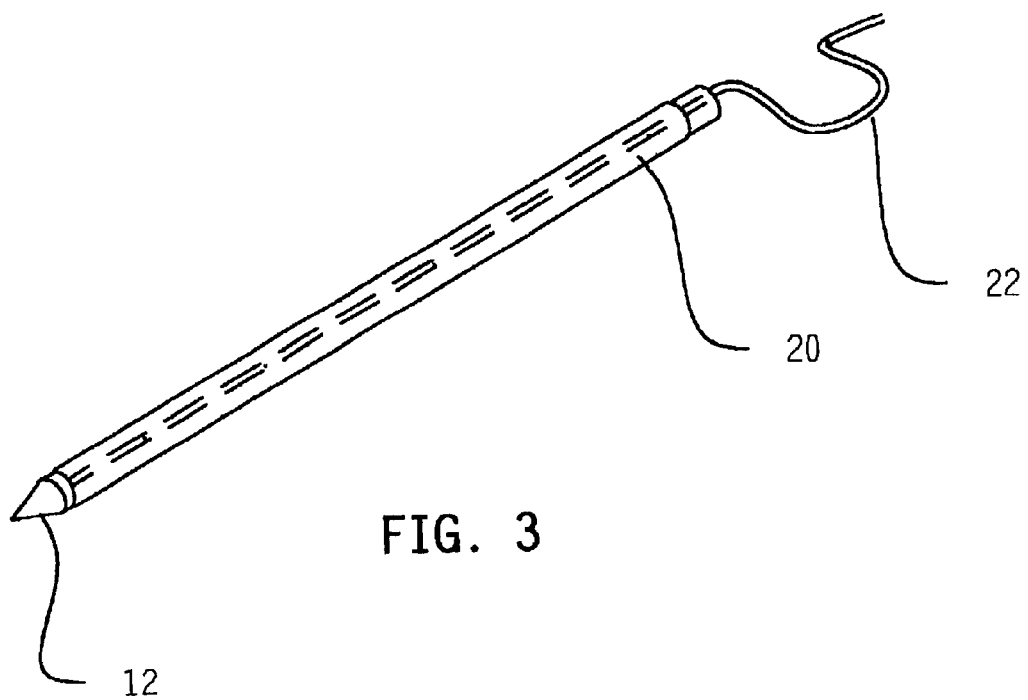
FIG. 3 shows the dissecting balloon in its uninflated configuration.

A malleable metal cannula 10 having an internal stylet 12 is first inserted into the body percutaneously (FIG. 1) and is guided fluoroscopically until the cannula lies along either the lamina of the transverse processes or the spinal elements to be fused (FIG. 2). The stylet is then removed, leaving the cannula in place. A generally cylindrical inflatable balloon 20 (FIG. 3), having an inflatable length approximating the distance between the vertebrae to be fused, is then inserted through the cannula.

Figure 4:
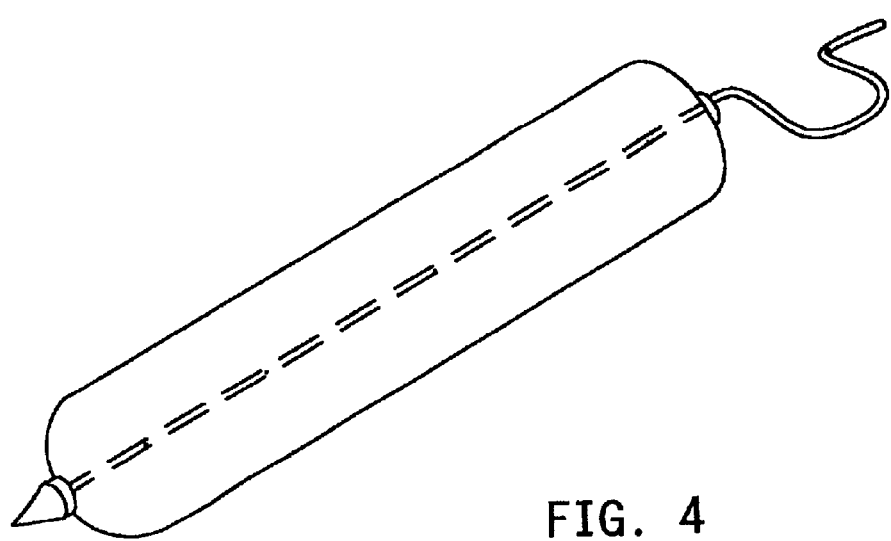
FIG. 4 shows the dissecting balloon in its inflated configuration.
Figure 5:
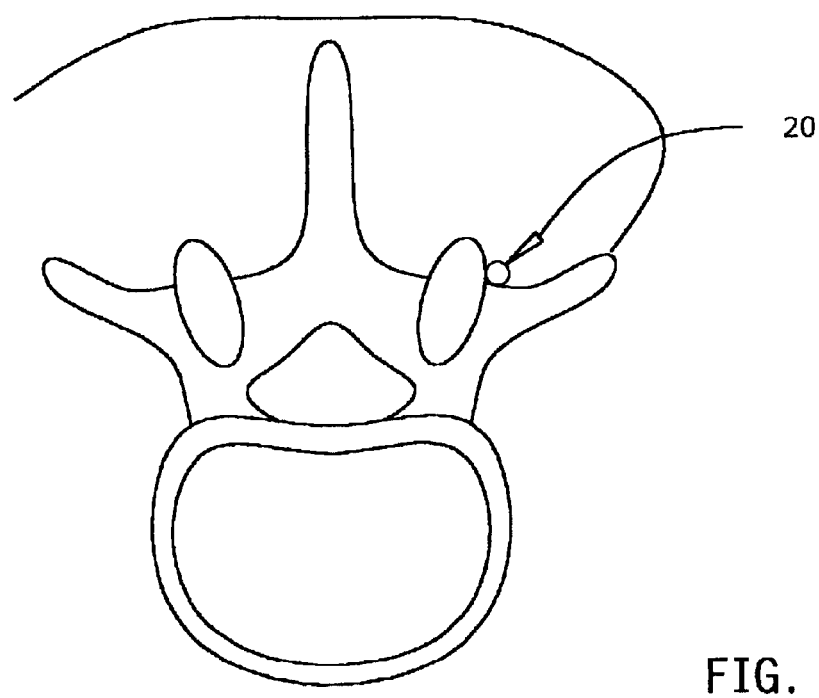
FIG. 5 is an axial view of the spine with the dissecting balloon in its uninflated configuration.
Figure 6:
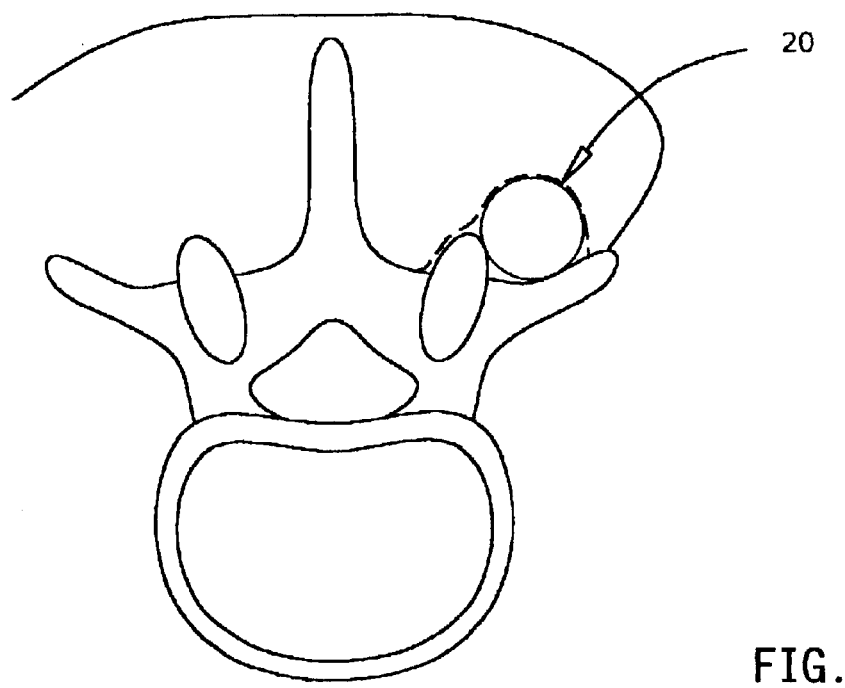
FIG. 6 is an axial view of the spine with the dissecting balloon in its inflated configuration.

The cannula 10 is then partially withdrawn, leaving the balloon in place along the spinal elements (FIG. 5). Next, the cylindrical balloon 20 is inflated (FIGS. 4, 6) by passing air or gas under pressure to the balloon via conduit 22. The expansion of the balloon elevates and dissects the muscle from either the lamina or the transverse processes, depending on the desired site for fusion. Once the muscle has been sufficiently separated from the bone, the balloon 20 is deflated and slid out through the metal cannula 10.

Figures 7, 8:
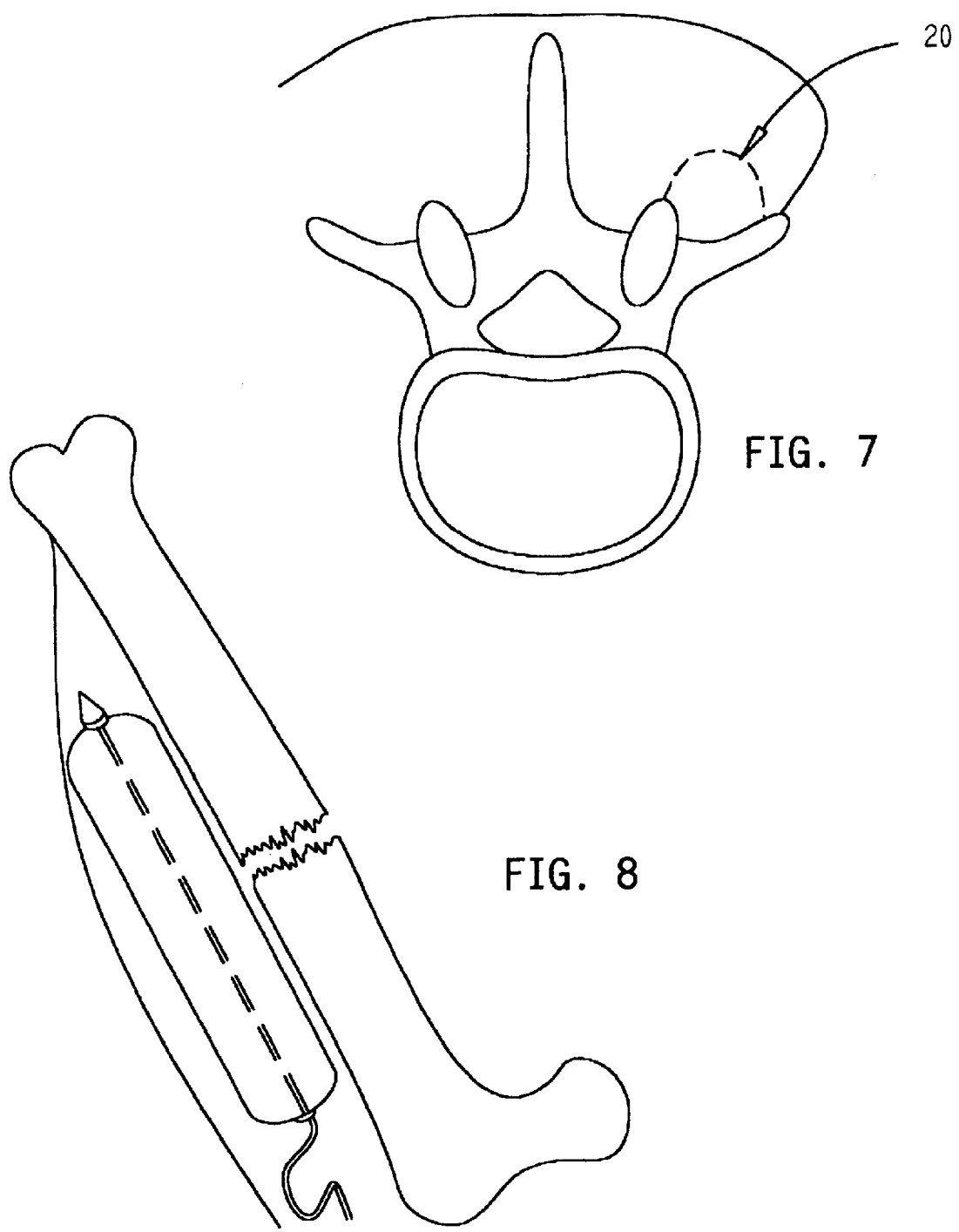
FIG. 7 is an axial view of the spine, illustrating the surgical site following deflation and withdrawal of the balloon.
FIG. 8 is a lateral view of a femur, with an inflated dissecting balloon along side in the vicinity of a fracture, retracting muscle tissue from the bone.

The potential space formed by the dissecting balloon is then insufflated with carbon dioxide or other inert gases to elevate the muscle away from the spinal vertebra. This allows for the formation of a cavity which can be accessed percutaneously with an endoscope and various surgical instruments necessary to perform the fusion procedure. The gas is then evacuated upon completion of the surgical procedure. The tissues return to their original position (FIG. 7) thereafter.

The method and implements described above allow the performance of a completely percutaneous surgical fusion procedure and they eliminate the need for a long and painful surgical incision, as well as avoiding the attendant muscle-damaging dissection techniques presently employed in posterior and posterolateral spinal fusion procedures.

While the dissection technique has been described with respect to a spinal operation, it should be evident that this technique may be used along other bones, for example, the femur (FIG. 8), the humerus, or the tibia.

Since the invention is subject to modifications and variations, it is intended that the foregoing description and the accompanying drawings shall be interpreted as only illustrative of the invention defined by the following claims.

I claim:

1. A method of dissecting muscle tissue from an adjacent bone, said method comprising steps of inserting an elongated dissection balloon into a cannula, inserting the cannula containing the balloon between the bone and the tissue, partially withdrawing the cannula, leaving the dissection balloon in place along the bone, inflating the dissection balloon to separate the muscle tissue from the bone, deflating the dissection balloon, and withdrawing the dissection balloon through the cannula.

2. A method of performing percutaneous, posterolateral spinal fusion, said method comprising steps of separating muscle and tissue from bone in a zone extending along a portion of the spine, insufflating an inert gas to elevate and maintain the tissue separation from bone, thereby forming a cavity, and accessing the formed cavity with percutaneous surgical instruments.

3. A method of performing percutaneous instrumented repair a fractured bone, said method comprising steps of inserting an elongated dissection balloon into a cannula, inserting the cannula containing the balloon between the bone and adjacent tissue, partially withdrawing the cannula, leaving the balloon in place along the bone and bridging the fracture site, inflating the dissection balloon to separate the tissue from the bone, repairing said bone, deflating the dissection balloon, and withdrawing the dissection balloon through the cannula.

* * * * *